United States Patent [19]

Zimmerman et al.

[11] Patent Number: 4,545,991

[45] Date of Patent: Oct. 8, 1985

[54] DIFFICIDIN AND DERIVATIVE ANTIBACTERIALS

[75] Inventors: Sheldon B. Zimmerman, Springfield; Kenneth E. Wilson, Westfield; Richard L. Monaghan, Somerset, all of N.J.; Sagrario M. Del Val; Maria I. M. Fernandez, both of Madrid, Spain; Otto D. Hensens, Red Bank, N.J.; James E. Flor, Bridgewater, N.J.; Cheryl Deriso, Avenel, N.J.

[73] Assignee: Merck & Co., Inc., Rahway, N.J.

[21] Appl. No.: 503,951

[22] Filed: Jun. 13, 1983

[51] Int. Cl.$^4$ .................. A61K 31/665; C07F 9/16
[52] U.S. Cl. ................................ 514/100; 435/53; 549/5
[58] Field of Search ..................... 549/5; 424/203

[56] References Cited

U.S. PATENT DOCUMENTS 3,767,799  10/1973  Vertesy et al. ............... 424/122

FOREIGN PATENT DOCUMENTS 1323833  7/1973  United Kingdom .

OTHER PUBLICATIONS

Prave, P. et al., J. Antibiotics 25 (1): pp. 1-3, 1972.
Vertasy, Laszlo, J. Antibiotics 25 (1): pp. 4-10, 1972.
Nesemann, G. et al., Naturwissenschafter 59 (2): pp. 81-82, 1972.

Primary Examiner—Richard L. Raymond

Attorney, Agent, or Firm—Thomas E. Arther; Raymond M. Speer; Hesna J. Pfeiffer

[57] ABSTRACT

Difficidin and derivative antibacterial compounds of the formula:

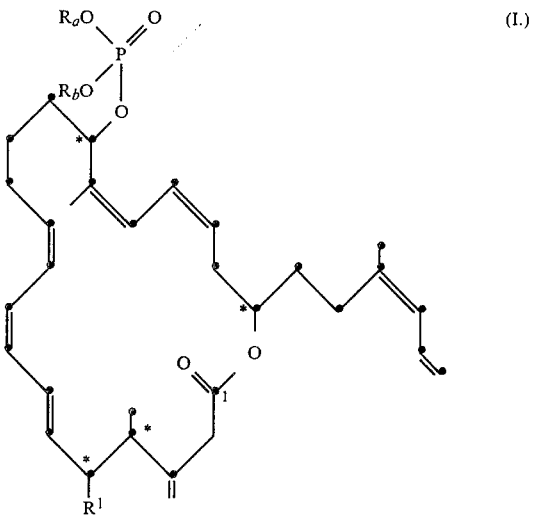

(I.)

where $R_a$ and $R_b$ are members independently selected from the group consisting of hydrogen; alkali metal and alkaline earth metal cations; ammonium; and substituted ammonium; and $R^1$ is hydrogen or hydroxy.

5 Claims, 2 Drawing Figures

Fig. 1

Fig.2

DIFFICIDIN AND DERIVATIVE ANTIBACTERIALS

BACKGROUND OF THE INVENTION

1. Field of the Invention

The present invention relates to a novel antibacterial compound referred to herein generally as "difficidin", and derivative compounds, and to a process for preparing, isolating, and purifying said compounds. As employed herein, the coined term "difficidin" refers to the compound of Formula I below wherein $R^1$ is hydrogen, and $R_a$ and $R_b$ have the recited meanings, thus affording various salt forms thereof. Correspondingly, the term "oxydifficidin", as used herein, refers to the compound of Formula I below wherein $R^1$ is hydroxy, and $R_a$ and $R_b$ have the indicated meanings. The novel antibacterial compounds are obtained by microbiological cultivation of *Bacillus subtilis*, MB 3575, and MB 4488 deposited with the American Type Culture Collection, Rockville, Md. under the designations ATCC 39374 and 39320, respectively.

The novel antibacterial compounds of the present invention, difficidin and derivative compounds, are broad spectrum antibacterials with good potency against aerobic microorganisms and exceptional potency against anaerobic microorganisms. They also exhibit good in vitro activity against microorganisms that have developed resistance to conventional antibacterials. They may be used parenterally in the treatment of gram positive and gram negative bacterial infections.

2. Brief Description of the Prior Art

Proticin is a known antibacterial compound which has been described as a phosphorous-containing, strongly unsaturated amorphous compound with broad activity spectrum, especially against gram negative pathogens. It is said to have been produced by fermentation of a strain identified as a form of *Bacillus licheniformis*. A more detailed description of its preparation, characteristics, and antibacterial activity may be found in the following references: (1) Präve, P. et al., J. Antibiotics 25 (1): 1-3, 1972; (2) Vertesy, L., J. Antibiot. 25 (1): 4-10, 1972; (3) Nesemann, G., et al., Naturwissenschaften 59 (2): 81-82, 1972; (4) Ger. Offen. No. 2,035,812 (Vertesy. L. et al.), "Proticin from *Bacillus licheniformis*", Farbwerke Hoechst A.-G., 18 July 1970; and (5) Brit. 1,350,271, "Proticin Production by *Bacillus licheniformis* fermentation," Farbwerke Hoechst A.-G., Apr. 18, 1974. (ref. Chem. Abstracts 81: 48531y, p 30b, 1974).

However, despite the repeated reference to the specific antibiotic compound proticin, the above references fail to characterize any single compound, and the spectral data provided therein is consistent with a number of possible compounds. Sine Vertesy Reference (2) above describes the presence of a methyl group at only one of the double bonds, whereas the compounds of the present invention have two such methyl groups, it has been concluded that the novel antibacterial compound of the present invention, wherein $R^1$ is hydroxy (oxydifficidin) is chemically distinct from the so-called proticin, described in the above references. On the other hand, the novel antibacterial compound of the present invention wherein $R^1$ is hydrogen (difficidin) is readily distinguished from the compound(s) of the references since it has a different molecular weight.

Chemically, difficidin is a 22-membered macrocyclic polyene lactone phosphate ester with asymmetric centers at C4, C5, C15 and C21, as illustrated by Formula I.

As can be seen, there are two chief compounds within Formula I. One compound is that wherein $R^1$ is hydrogen, which as already mentioned, shall be referred to hereinafter as "difficidin"; and the other compound is that wherein $R^1$ is hydroxy, which shall be referred to hereinafter as "oxydifficidin".

Biologically, difficidin has been found to be more potent than oxydifficidin against aerobic microorganisms such as *Pseudomonas aeruginosa* and *Staphyloccocus aureus*. In most cases it was found to be four times more effective against *S. aureus*, *Ps. aeruginosa*, *Salmonella typhimurium*, *Proteus*, and *Serratia marcescens* than oxydifficidin. Difficidin and oxydifficidin are also active against a wide spectrum of anaerobic bacteria.

DETAILED DESCRIPTION OF THE INVENTION AND PREFERRED EMBODIMENTS

In accordance with the present invention there is provided the novel antibacterial compound, difficidin, and its derivatives of the formula:

where $R_a$ and $R_b$ are members independently selected from the group consisting of hydrogen; alkali metal and alkaline earth metal cations; ammonium; and substituted ammonium; and $R^1$ is hydrogen or hydroxy.

The ammonium cation may be substituted in known manner, preferably with lower alkyl, for example.

Difficidin has been prepared and utilized as the potassium phosphate salt, being a changing equilibrium of the mono- and di-potassium salts. This salt form has been employed due to its ease of preparation and the possible instability of the acid form, where $R_a = R_b = H$, which exists at a low pH.

Difficidin and its derivatives may be prepared by microbiological cultivation of *Bacillus subtilis*, MB 3575 and MB 4488 deposited with the American Type Culture Collection, Rockville, Md., from which it is available without restriction under the accession numbers ATCC 39374 and 39320, respectively.

The bacillus, or its variants and mutants may be cultivated in accordance with well known microbiological processes, either on agar slant tubes, or under submerged conditions in Erlenmeyer flasks or fermentors, utilizing nutrient media or nutrient solutions generally employed for cultivating microorganisms.

In the present invention, difficidin and its derivatives are produced during cultivation of the microorganism, for example, *Bacillus subtilis* ATCC 39320 at a temperature of about 28° C., under aerobic condition. The composition of the nutrient medium may be varied over a wide range. The essential assimilable nutrient ingredients are; a carbon source, a nitrogen source, a source of inorganic elements including phosphorus, sulfur, magnesium, potassium, calcium and chlorine. Cultivation is most productive under neutral pH conditions, preferably from about 6.0 to 7.0.

Typical sources of carbon include, glucose, dextrin, starches, glycerol and the like. Typical nitrogen sources include vegetable meals (soy, cottonseed, corn, etc.), meat flours or animal peptones, distillers solubles, casamino acids, yeast cells, various hydrolysates (casein, yeast, soybean, etc.), yeast nucleic acids and amino acids.

Mineral salts such as the chlorides, nitrates, sulfates, carbonates and phosphates of sodium, potassium, ammonium, magnesium and calcium provide a source of essential inorganic elements. The nutritive medium may also contain a number of trace elements such as iron, copper, manganese, zinc and cobalt.

If excessive foaming is encountered during the cultivation, antifoaming agents such as vegetable oils, lard oil and polypropylene glycol may be added to the fermentation medium prior to, or during the course of the fermentation. The maximum yield of difficidin can be achieved within from about 20 to 120 hours, and is culture dependent. The inoculum for the fermentation can be provided from suspensions, slants, frozen cells or freeze-dried preparations.

In addition to the conventional cultivation processes described above, there may also be employed continuous processes, such as that described in *Methods in Microbiology*, Vol. 2, Academic Press, London—New York, 1970, pp. 259–328. In such systems the bacillus can be maintained for extended periods of time in a steady state without spontaneous mutations or other degenerations becoming evident.

It is to be understood that for the production of difficidin and its derivatives, the present invention is not limited to the use of *Bacillus subtilis* ATCC 39374 or 39320. It is especially desired and intended to include the use of natural or artificial mutants produced from the described organisms, or other variants of *Bacillus subtilis* ATCC 39374 or 39320 as far as they can produce difficidin and its derivatives. The artificial production of mutant *Bacillus subtilis* may be achieved by a conventional operation such as X-ray or ultraviolet (UV) radiation, or by the use of chemical mutagens such as; nitrogen mustards, nitrosoguanidine, camphor and the like, or by means of recombinant DNA technology.

MORPHOLOGICAL AND PHYSIOLOGICAL CHARACTERISTICS OF BACILLUS SUBTILIS ATCC 39320

The morphological and physiological properties of ATCC 39320 are as follows:

Morphology: gram positive, non-vacuolated vegetative rods with rounded ends; average size 0.9×2.3–3.6μ; occurring singly. Rods are motile. Spores are produced under aerobic conditions. Spores are 0.5×1.0μ (average size), oval to cylindrical, predominantly central, sporangia not swollen.

Colonial appearance: flat, round with irregular edge, surface dull, edge becoming opaque as colony ages. Dull, wrinkled entire pellicle on surface of broth. No pigmentation on trypticase soy agar. Growth at 28° C., 37° C., no growth at 60° C.

Positive reactions: Catalase, Voges-Proskauer, gelatin, nitrate reduction, utilization of citrate, acid from glucose, arabinose, mannitol, xylose, sorbitol and sucrose, hydrolysis of starch.

Negative reactions: urease, indole, utilization of propionate, arginine dihydrolase, acid from rhamnose and mellibiose, no growth in anaerobic agar (stabs or plates incubated in anaerobic jars), no growth in glucose broth or nitrate broth under anaerobic conditions.

Comparison with culture descriptions in Bergey's *Manual of Determinative Bacteriology*, Eighth Edition, Williams & Wilkins, 1974, and Gordon, R. E., Haynes, W. C. and Pang, C. H. (1973), The Genus Bacillus, Agriculture Monograph No. 427, U.S. Department of Agriculture, Washington, D.C., indicate that MB 4488/ATCC 39320 is a strain of known species *Bacillus subtilis*.

MORPHOLOGICAL AND PHYSIOLOGICAL CHARACTERISTICS OF BACILLUS SUBTILIS ATCC 39374

The morphological and physiological properties of ATCC 39374 are the same as those indicated above for ATCC 39320, except with respect to the appearance of the colonies of the microorganism, which are as follows:

Colonial appearance: At 24 hours, raised, round, mucoid. As colony ages, edge becomes dry, opaque and irregular. Central mucoid area continues to dry, becoming opaque and wrinkled.

Dull, wrinkled entire pellicle on surface of broth. No pigmentation on trypticase soy agar. Growth at 28° C., 37° C., no growth at 60° C.

PRODUCTION OF DIFFICIDIN AND ITS DERIVATIVES

A. A process for preparing the antibacterial compound difficidin and its derivatives, or one of their salts, but in which oxydifficidin is produced in greater proportion, involves the cultivation of microorganisms which form difficidin and its derivatives and belong to the strain of *Bacillus subtilis* ATCC 39320 at a temperature ranging from 20° to 40° C. for from 24 to 120 hours by means of an aqueous nutrient solution which contains a source of carbon, a source of nitrogen, nutrient salts and trace elements, until the nutrient solution contains considerable amounts of difficidin and its derivatives, after which the difficidin and its derivatives are isolated from the culture and converted, if desired, into a salt with a pharmaceutically acceptable base.

During cultivation the pH value of the nutrient medium changes from neutral to slightly acidic; in general the addition of a buffer solution is not necessary, although one could be employed as a precaution. The cultivation is suitably stopped after 2 to 4 days, since a favorable yield is obtained after this period; the nutrient solution then contains a substantial amount of oxydifficidin. It has been found that the ATCC 39320 culture produces a preponderance of oxydifficidin, as compared to difficidin, but that the overall titer is lower than with the ATCC 39374 culture described below.

B. Another, and preferred, process for preparing the antibacterial compound difficidin and its derivatives, or one of their salts with a pharmaceutically acceptable base, but in which difficidin is produced in greater proportion, involves the cultivation of microorganisms which form difficidin and its derivatives and belong to the strain of *Bacillus subtilis* ATCC 39374 at a temperature ranging from 20° to 40° C. for from 24 to 120 hours by means of an aqueous nutrient solution which contains a source of carbon, a source of nitrogen, nutrient salts and trace elements, including particularly cobalt, until the nutrient solution contains considerable amounts of difficidin and its derivatives after which the difficidin and its derivatives are isolated from the culture and converted, if desired, into a salt with a pharmaceutically acceptable base.

As already mentioned, the process utilizing the strain of *Bacillus subtilis* ATCC 39374 is also preferred because it has been found to produce greater proportions of difficidin than oxydifficidin and higher titers than the *Bacillus subtilis* ATCC 39320 microorganism utilized in the process described under "A" above.

It has been found that the addition of cobalt, in amounts of for example 0.1 g/l, causes preferential production of difficidin by the microorganism, to the extent of as much as a 3:1 weight ratio to the amount of oxydifficidin produced. Various water soluble salts of cobalt may be employed, for example cobalt chloride hexahydrate, which is preferred.

Similarly, it has been found that the addition of phosphate, in amounts of for example 100 p.p.m., in the presence of cobalt, causes preferential production of difficidin by the *Bacillus subtilis* culture, as compared to the production of oxydifficidin. On the other hand, preferential production of oxydifficidin can be accomplished by addition of manganese, for example, manganese chloride tetrahydrate, in amounts of, for example, 0.025 g/l. However, these findings are preliminary in nature and are included only as an indication of potential advantageous manipulation of the culture medium for the purpose of affecting production of either difficidin or oxydifficidin, as may be preferred.

ISOLATION OF DIFFICIDIN AND ITS DERIVATIVES

In order to isolate difficidin and its derivatives, the culture of the bacillus may first be clarified by centrifugation, which, however, results in a considerable proportion of difficidin and its derivatives remaining in the cell mass. This crude product may be purified by chromatography using an appropriate adsorbent such as polymeric organic based resins, such as XAD-2 and HP-20 resins, and polymeric silicic acid based resins, such as LiChroprep RP-18 resin and Watman ODS resins, both of which are silica with a chemically bonded outer layer of $C_{18}H_{37}$ residues. Difficidin and its derivatives are eluted from the adsorbent with suitable polar solvents or mixtures of solvents, after which aqueous extraction of difficidin and its derivatives is carried out. The difficidin and oxydifficidin are then separated from each other and structurally related components by HPLC.

ANTIBACTERIAL ACTIVITY

Using standard in vitro assay techniques, minimal inhibitory concentrations (MIC) have been determined for difficidin and oxydifficidin against a number of bacteria. The results obtained are illustrated in Table I below.

TABLE I

| | MIC (μg/ml) Range | |
|---|---|---|
| Organism ($10^6$ CFU) | Oxy-difficidin | Difficidin |
| *Staphylococcus aureus* (3)* | 32–128 | 8–16 |
| *Streptococcus faecalis* (1) | 128 | 128 |
| *Escherichia coli* (4) | 4–16 | 8 |
| *Salmonella typhimurium* (1) | 32 | 8 |
| *Enterobacter* (3) | 32–64 | 8–16 |
| *Klebsiella pneumoniae* (2) | 8 | 8 |
| *Proteus* (3) | 2–32 | 0.5–8 |
| *Pseudomonas aeruginosa* (3) | 16–32 | 8 |
| *Serratia marcescens* (1) | 16 | 4 |

*number of strains tested.

Further evaluations of the antibacterial spectrum of difficidin and oxydifficidin were undertaken, especially as compared to the antibacterial spectrum of the valuable antibiotic cefoxitin, which is well known for its wide spectrum of antibacterial activity. An in vitro agar dilution assay was used, inoculum $10^6$ CFU per spot. Table II below illustrates the results obtained for various aerobic bacteria, and Table III illustrates the results obtained for various anaerobic bacteria.

TABLE II

| | MIC (μg/ml) | | |
|---|---|---|---|
| Aerobic Bacteria | Oxy-difficidin | Difficidin | Cefoxitin |
| *S. aureus* $Gm^R Meth^R$ | 32.0 | 8.0 | >128 |
| *S. aureus* | >128.0 | 16.0 | 2 |
| *S. aureus* | 32.0 | 8.0 | 2 |
| *Strep. faecalis* | >128.0 | >128.0 | >128 |
| *E. coli* TEM 2+ | 16.0 | 8.0 | 4 |
| *E. coli* TEM 2+DC 2 | 8.0 | 8.0 | 1 |
| *E. coli* DC 2 | 4.0 | 8.0 | 1 |
| *E. coli* | 4.0 | 8.0 | >128 |
| *Sal. typhimurium* | 32.0 | 8.0 | 8 |
| *Ent. cloacae* P99+ | 32.0 | 16.0 | >128 |
| *Ent. cloacae* P99− | 64.0 | 8.0 | 16 |
| *Ent. aerogenes* | 32.0 | 8.0 | >128 |
| *K. pneumoniae* K1+ | 8.0 | 8.0 | 4 |
| *Prot. vulgaris* | 8.0 | 0.5 | 16 |
| *Prot. morganii* $Sm^R$ | 2.0 | 2.0 | 16 |
| *Prot. mirabilis* $Gm^R$ | 32.0 | 8.0 | 32 |
| *Ps. aeruginosa* RPL 11+ | 16.0 | 8.0 | >128 |
| *Ps. aeruginosa* | 32.0 | 8.0 | >128 |
| *Ps. aeruginosa* | 32.0 | 8.0 | >128 |
| *Ser. marcescens* | 16.0 | 4.0 | 64 |

TABLE III

| | MIC (μg/ml) | | |
|---|---|---|---|
| Anaerobic Bacteria | Oxy-difficidin | Difficidin | Cefoxitin |
| *Actinomyces naeslundii* | 64 | >128 | 0.015 |
| *Eubacterium limosum* | >128 | >128 | 0.25 |
| *Propionibacterium acnes* | 8 | 1 | ≦0.008 |
| *Peptostreptococcus anaerobius* | 0.06 | 0.06 | ≦0.008 |
| *Clostridium perfringens* NCCLS control strain | >128 | >128 | 0.5 |
| *C. ramosum* | 2 | 2 | 4 |
| *C. difficile* Clind$^r$, Fox$^r$ | 0.06 | 0.125 | 64 |
| *C. difficile* Fox$^r$ | 0.06 | 0.06 | 128 |
| *Bifidobacterium dentium* Fox$^r$ | >128 | 32 | 4 |
| *Bacteriodes fragilis* Metr$^r$, Pen$^r$ | 0.25 | 0.125 | 2 |
| *B. fragilis* Pen$^r$ | 0.125 | 0.125 | 8 |
| *B. fragilis* Clind$^r$ Fox$^r$ Tet$^r$ | 0.25 | 0.25 | 32 |
| *B. fragilis* | 0.25 | 0.06 | 4 |

TABLE III-continued

| Anaerobic Bacteria | MIC (μg/ml) | | |
|---|---|---|---|
| | Oxy-difficidin | Difficidin | Cefoxitin |
| NCCLS control strain | | | |
| *B. distasonis* Pen$^r$ Fox$^r$ Clind$^r$ | 0.06 | 0.06 | 16 |
| *B. distasonis* Pen$^r$ Fox$^r$ | >128 | >128 | 64 |
| *B. ovatus* Pen$^r$ | 0.25 | 0.125 | 8 |
| *B. thetaiotaomicron* Clind$^r$ | 0.25 | 0.25 | 16 |
| *B. thetaiotaomicron* Clind$^r$, NCCLS control strain | 0.25 | 0.06 | 16 |
| *Fusobacterium mortiferum* Fox$^r$ | 0.125 | 0.03 | 16 |
| *Veillonella alcalescens* | 0.06 | 0.25 | 0.5 |

The antibacterial efficacy of difficidin and its derivatives was further determined in standard mouse protection tests. An experimental systemic infection was produced in CD1 female mice (Charles River Breeding Laboratories, Wilmington, MA) by the intraperitoneal injection of a suitably diluted broth culture of *Klebsiella pneumoniae* MB 4005. The test antibacterial compounds and the control drug (streptomycin) were administered parenterally (intraperitoneally) immediately after infection and again 6 hours later. At least 4 fourfold dilutions of each agent were tested. There were 5 mice at each dose level. All mice were observed for a period of seven days after which the median effective dose (ED$_{50}$) was calculated by the method of Knudsen and Curtis (Knudsen, L. F. and J. M. Curtis. J. Amer. Statist. Assn. 42: 282–296, 1947). Under the conditions of the test, all infected untreated mice died within 48 hours.

Mice were protected by the administration of the test antibacterial compounds or streptomycin at the median effective doses shown in Table IV below.

TABLE IV

| Test No. | Antibiotic | ED$_{50}$ mg/kg × 2 i.p. doses | MIC μg/ml |
|---|---|---|---|
| 1 | Oxydifficidin | 12.25 | 8 |
| | Streptomycin | 0.38 | |
| 2 | Oxydifficidin | 14.85 | 40 |
| | Streptomycin | 1.41 | |
| 3 | Difficidin | 1.56 | 8 |
| | Streptomycin | 0.38 | |

These data show that all test antibacterial compounds were effective in protecting mice from an otherwise lethal infection with *Klebsiella pneumoniae*.

From the foregoing in vitro and in vivo data it is expected that an effective antibacterial amount of difficidin and its derivatives would be on the order of 5 mg/kg to 20 mg/kg in mammals. Difficidin and its derivatives are effective for treatment of gram negative and gram positive infections as described above, and may be administered intravenously, intramuscularly, or subcutaneously, either alone or in combination with a pharmaceutical carrier. The ultimate choice of route and dose should be made by an attending physician and based upon the patient's unique condition.

Combinations of difficidin and its derivatives with appropriate pharmaceutical carriers are accomplished by methods well known to the pharmacist's art. For purposes of subcutaneous (s.c.) administration, solutions of difficidin and its derivatives are generally employed, for example, sterile aqueous or alcoholic solutions. Such solutions should be suitably buffered if necessary and the liquid diluent may first be rendered isotonic with saline or glucose. These aqueous and alcoholic solutions are also suitable for intravenous (i.v.) injections.

The following examples illustrate the preparation and isolation of difficidin and oxydifficidin from *Bacillus subtilis* ATCC 39320 and ATCC 39374.

EXAMPLE 1

Production of Difficidin and Oxydifficidin Using ATCC 39320

| | | | |
|---|---|---|---|
| 1. "A" Stage | Culture MB 4488, lyophilization tubes, is maintained in the lyophilized state in a 1.0 ml ampule containing 0.15 ml of a skim milk suspension of the culture. | | |
| 2. "B" Stage | | | |
| Vessel: | 250 ml 3-baffled Erlenmeyer flask containing 50 ml medium per flask. | | |
| Medium: | | | Wt/Vol |
| | Dextrose | | 1 g/l |
| | Soluble Starch | | 10 g/l |
| | Beef Extract | | 3 g/l |
| | Ardamine pH | | 5 g/l |
| | NZ-Amine Type E | | 5 g/l |
| | MgSO$_4$ 7 H$_2$O | | 0.05 g/l |
| | 1.34 M Phosphate Buffer | | 0.02% Vol/vol |
| | CaCO$_3$ (After pH Adjustment to 7.0–7.2) | | 0.05% |
| | Phosphate Buffer | | |
| | KH$_2$PO$_4$ | | 91 g/l |
| | Na$_2$HPO$_4$ | | 95 g/l |
| Inoculum: | Contents of one Lyo tube into each "B" flask. | | |
| Incubation: | 24 hours at 28° C. on a rotary shaker with a 2" throw rotating at 220 RPM. | | |
| Sterility: | Streak plates and gram stain. | | |
| 3. "C" Stage | | | |
| Vessel: | 2 liter 3-baffled Erlenmeyer flask containing 500 ml medium. | | |
| Medium: | Same as "B" stage. | | |
| Inoculum: | 10 ml from "B" stage. | | |
| Incubation: | Same as "B" stage. | | |
| Sterility: | Same as "B" stage. | | |
| 4. "E" Stage | | | |
| Vessel: | 750 liter stainless steel fermentor. | | |
| Medium: | Dextrin | | 40 g/l |
| | Solulac | | 7 g/l |
| | Ardamine YEP | | 5 g/l |
| | Cobalt Chloride | | 50 mg/l |
| | Polyglycol 2000 | | 1 ml/l |
| | Pre-sterile pH | | 7.3 |
| Sterilization: | 20 minutes at 121° C. | | |
| Inoculum: | 1 liter "C" stage. | | |
| Fermentor Volume A.I.: | 501 liters. | | |
| Temperature: | 28° C. | | |
| Airflow: | 5 CFM (30 hrs) then 6 CFM. | | |
| Agitation: | 130 RPM (12 hrs) then 110 RPM. | | |
| Pressure: | 13 PSI. | | |
| Defoamer: | Polyglycol 2000 | | |
| Cycle Time: | 92 hours. | | |
| Sterility: | Microscopic examination and streak plates at 28° and 37° C. | | |
| Physiology: | | | |

| Age (hrs) | pH | % Cell Volume | NH$_3$ | PO$_4$ | Difficidin Titer (μg/ml) |
|---|---|---|---|---|---|
| 0 | 6.5 | 4 | 55 | 380 | |
| 9 | 6.0 | 5 | 40 | 200 | |
| 21 | — | 14 | 80 | 210 | |
| 33 | 6.4 | — | 105 | 220 | |
| 45 | 6.4 | — | 70 | 250 | 10.8 |
| 57 | 6.3 | — | 15 | 180 | 7.9 |
| 69 | 6.4 | — | 10 | 210 | — |
| 81 | 6.0 | 4 | 25 | 250 | 7.4 |
| 93 | 6.0 | 2 | 65 | 275 | 6.6 |

EXAMPLE 2

Isolation and Purification of Difficidin and Oxydifficidin

A. Preliminary isolation of antibacterial complex

Approximately 420 L of whole broth (pH 5.9) from the fermentation batch described in Example 1 was harvested at 92 hours. The broth was clarified using a Sharples centrifuge. The 416 L of clarified broth was adjusted to pH 5.0 with 500 ml of 4N hydrochloric acid and then adsorbed onto 38 L of Rohm and Haas Amberlite XAD-2 resin at 4 L/min. The resin was washed at 4 L/min. with 120 L of cold, distilled deionized water. The antibacterial complex was eluted from the resin with 160 L of ethyl acetate at 4 L/min. The lower aqueous layer in the eluate was removed and discarded. The eluate was dried by agitation for 30 minutes over anhydrous sodium sulfate. The drying agent was removed by filtration and the filtrate was concentrated under vacuum to 2.65 L. A 1 liter portion of water was added to the concentrate and under gentle stirring the pH of the lower aqueous phase was adjusted to 8.5 with 130 ml of 2.5N sodium hydroxide. The mixture was stirred vigorously for 2 minutes. The layers were allowed to separate. The lower aqueous extract was decanted and the upper organic layer was extracted twice more, each time with 500 ml of water and sufficient 2.5N sodium hydroxide to bring the pH to 8.5 during extraction. The three aqueous extracts were combined and adjusted to pH 6.9. The extract volume was 2.4 L. The 2.1 L spent ethyl acetate solution contained 94 g of total solids.

Difficidin and oxydifficidin were present to various extents in both the aqueous extract and the spent ethyl acetate fraction. Step B below describes the isolation of difficidin and oxydifficidin from the spent ethyl acetate. Step C below describes the isolation of difficidin from the aqueous extract. Step D describes an alternative isolation procedure and corresponding analytical evaluation.

B. Isolation of Difficidin and Oxydifficidin

A 0.4 ml sample of 2.1 L spent ethyl acetate fraction from Step A above was evaporated to an oily residue and taken up in 0.7 ml of 7:3 methanol-0.01M potassium phosphate pH 7.0. A 0.4 ml aliquot of the solution was chromatographed in the same solvent at 28° C. on a Dupont Zorbax ODS column (4.6 mn ID×25 cm), 10 micron. The flow rate was 1 ml/min. and column effluent was monitored at 275 nm using a Laboratory Data Control Spectra Monitor I ultraviolet detector equipped with a 10 mm pathlength flow cell and a Honeywell Electronik 195 recorder. Eluate was collected in 0.5 ml fractions and assayed by agar disc diffusion against *Vibrio percolans* MB 1272. Table V summaries bioassay results.

The data in Table V show the presence of two distinct antibacterial substances in spent ethyl acetate. The activity in Fractions 11 and 12 is due to the antibacterial oxydifficidin. The activity in Fractions 61–65 is due to the antibacterial difficidin.

TABLE V

In vitro *Vibrio percolans* Bioassay Results of Column Fractions

| Fraction | Zone Diameter (mm)* | Peak Assign. and Elution Time | Component Assignment |
|---|---|---|---|
| 1–10 | 0 | Peak 1, 336 sec | Oxydifficidin |
| 11 | 23 | | |
| 12 | 19 | | |
| 61 | 12 | Peak 2, 1844 sec | Difficidin Component |
| 62 | 12 | | |
| 63 | 12 | | |
| 64 | 12 | | |
| 65 | 12 | | |
| 66–120 | 0 | | |

*agar disc diffusion, 40 μl on ⅜" disc

C. Isolation of Antibacterial Difficidin—Method 1

The 2.4 L of combined aqueous extract (66 g total solids) from Step A above was concentrated to 2.1 L to remove most of the dissolved ethyl acetate. The concentrate was diluted with 0.22 L of 1M potassium phosphate pH 7.0 and adsorbed at 50 ml/min. on 1 liter of Mitsubishi Diaion HP-20 resin. The resin was washed successively with 3 L of distilled water, 3 L of 1:1 methanol-0.1M potassium phosphate pH 7.0, 3 L of 65:35 methanol-phosphate buffer, and 3 L of 9:1 methanol-distilled water. The antibacterial complex was eluted at 50 ml/min. with 3.9 L of methanol, collected as a 1.45 L forerun fraction and a 2.45 L rich cut. The forerun was enriched in oxydifficidin while the rich cut was enriched in difficidin. The rich cut (0.55 g total solids) was concentrated to 50 ml and diluted with 116 ml of 0.1M potassium phosphate pH 7.0. The solution was charged on a 74 ml column of E. Merck LiChroprep RP-18, 25–40 micron resin at 5 ml/min. The column was successively developed with methanol-water mixtures of increasing methanol concentration (Table VI). The flow rate was 5 ml/min. and fractions were 7.5 ml each.

TABLE VI

Chromatography of Crude Difficidin Component on LiChroprep RP-18

| Fraction | Solvent | Volume |
|---|---|---|
| 1–27 | 1:1 methanol-water | 7.5 ml/fraction |
| 28–60 | 55:45 methanol-water | 7.5 ml/fraction |
| 61–95 | 60:40 methanol-water | 7.5 ml/fraction |
| 96–130 | 65:35 methanol-water | 7.5 ml/fraction |
| 131–190 | 70:30 methanol-water | 7.5 ml/fraction |

Based on HPLC analysis and bioassay of fractions, an antibacterial eluted in Fractions 109–121 which exhibited the same HPLC retention time as Peak 2 (difficidin component) of Table V. Fractions 109–121 were combined as crude difficidin component rich cut.

The rich cut was concentrated to 8.2 ml and diluted with 0.9 ml of 1M sodium citrate pH 5.4 and 6.1 ml of methanol. The solution was adsorbed at 2 ml/min. onto a 17 ml column of E. Merck LiChroprep RP-18 resin, 25–40 micron in 4:6 methanol-0.1M sodium citrate pH 5.5. The column was washed at the same flow rate with 30 ml of 4:6 methanol-citrate buffer. The column was then developed with 75:25 methanol-citrate (Fractions 1–35) and 8:2 methanol-citrate (Fractions 36–70). All fractions were 2 ml. Based on TLC and UV analysis, Fractions 42–65 were combined and concentrated to 6 ml. The resulting white suspension was diluted with 5 ml of 0.1M potassium phosphate pH 7.2 and sufficient methanol (7 ml) to redissolve the insoluble material. The solution was desalted in the following manner. The solution was adsorbed on 8 ml of LiChroprep RP-18 resin in 3:7 methanol-0.1M potassium phosphate pH 7.0. The resin was washed successively with 24 ml of 3:7 methanol-phosphate buffer and 24 ml of 3:7 methanol-distilled water. The difficidin component was eluted with 30 ml of 9:1 methanol-distilled water. The eluate was analyzed by HPLC using a Dupont Zorbax ODS column (4.6 mm ID×25 cm) at ambient temperature in 81:19 methanol-0.1M sodium citrate pH 5.5. The flow rate was 2 ml/min. Approximately 94% of the UV absorbance of the eluate at 275 nm was attributable to difficidin component (retention time 379 sec.). An impurity with retention time 418 seconds accounted for the remaining 6% of 275 nm absorbance. The impurity was removed by careful chromatography on LiChroprep RP-18 resin. Thus the above 30 ml eluate was concentrated to remove methanol and diluted with 1M sodium citrate pH 5.4 and methanol to 8 ml and a final solvent composition of 4:6 methanol-0.1M sodium citrate. The solution was charged on 17 ml of LiChroprep RP-18 resin. The column was eluted at 2 ml/min. successively with 75:25 methanol-0.1M sodium citrate pH 5.5 (Fractions 1-31, 2 ml each) and 8:2 methanol-citrate (Fractions 32-72, 2 ml each). Based on HPLC analysis Fractions 41-54 were combined as Rich Cut 1. The pH of the rich cut was increased 1.5 units with dilute sodium hydroxide. Off-fractions 55-72 were combined, concentrated to a solvent composition of 4:6 methanol-0.1M citrate and chromatographed as described above on 17 ml of LiChroprep RP-18. Appropriate fractions were combined as Rich Cut 2. Solution pH was increased 1.5 units. Rich Cuts 1 and 2 were combined, concentrated to remove methanol and adjusted to pH 7.2 with 0.1M potassium phosphate pH 8.0. To the resulting 10 ml of cloudy solution was added sufficient methanol (7.5 ml) to clarify the sample. The solution was desalted by adsorption on 8 ml of LiChroprep RP-18 resin. The resin was washed successively with 50 ml of 3:7 methanol-0.1M potassium phosphate pH 7.0 and 30 ml of 3:7 methanol-distilled water. The resin was then eluted with 30 ml of 9:1 methanol-water. The eluate contained approximately 21 mg of substantially pure difficidin.

D. Isolation of Antibacterial Difficidin—Method 2

A 1.7 L aliquot of the 2.1 L spent ethyl acetate solution of Part A above was concentrated to an oil at 40° C. and diluted to 915 ml with 9:1 methanol-water. Insoluble material was removed by centrifugation. The clear centrifugate was adsorbed at 20 ml/min on a column of 600 ml of DEAE-Sephadex A-25 (acetate cycle), packed in 9:1 methanol-water. The resin was washed with 4 L of 9:1 methanol-water. Crude difficidin component was eluted from the resin with 3% ammonium chloride in 9:1 methanol-water during which a series of 100 ml fractions were collected. The 450 ml rich cut, Fractions 7-10, contained 160 mg of difficidin by HPLC assay. The rich cut was desalted by diluting with 916 ml of water and absorbing at 18 ml/min on 180 ml of Diaion HP-20 resin. The resin was washed successively with 600 ml of water, 600 ml of 0.1M potassium phosphate pH 7.5, and again 600 ml of water. Elution of the resin with methanol afforded a 208 ml antibiotic rich cut containing 1 g of total solids. The sample was concentrated to 100 ml, diluted with 233 ml of 0.05M potassium phosphate pH 7, and charged on a 190 ml column of LiChroprep RP-18 resin, 25-40 micron. The column was then eluted at 10 ml/min with 1:1 methanol-0.05M potassium phosphate pH7 (Fractions 1-40) followed by a linear gradient from 50% methanol to 90% methanol-buffer (Fractions 41-280). All fractions were 10 ml each. Based on HPLC assays and in vitro agar disc diffusion assays against *Vibrio percolans*, Fractions 222-237 were pooled. The 154 ml rich cut contained 115 mg of difficidin. The sample was diluted with 170 ml of 0.05M potassium phosphate pH 7 and adsorbed on a 95 ml Whatman Partisil M20 10/25 ODS-3 column (2.2 cm 1D×25 cm), 10 micron. The column was eluted at 10 ml/min successively with 65:35 methanol-0.05M potassium phosphate pH7 (Fractions 1-89), 70:30 methanol-buffer (Fractions 90-149), and 75:25 methanol-buffer (Fractions 150-230). All fractions were 5 ml each. Fractions 180-220 were combined and evaporated to 34 ml. Sufficient methanol (11 ml) was added to clarify the resulting milky suspension. The solution was adsorbed at 2 ml/min on 18 ml of Diaion HP-20 resin. The resin was washed with 40 ml of 3:7 methanol-water. The resin was eluted with methanol to afford a rich cut containing 83 mg of essentially pure difficidin, potassium salt. Lyophilization of the antibiotic from water gave a white amorphous solid, for which the analytical results described below were obtained.

PHYSICOCHEMICAL CHARACTERIZATION OF DIFFICIDIN soluble in water, lower alcohols such as methanol and ethanol;

pH of 0.1% by weight aqueous solution is 6.9;

| UV Spectrum (in methanol) | |
|---|---|
| λ max | $A_{1\ cm}^{1\%}$ |
| 235 nm | 866 |
| 263 nm | 316 |
| 273 nm | 415 |
| 283 nm | 328 |

MASS SPECTRAL DATA

Upon trimethylsilylation, the sample exhibited a molecular ion at m/z 688.3741 as a di-TMS derivative $(M^+.TMS_2)$ corresponding to the molecular formula $C_{31}H_{45}O_6P$: MW 544 (calc'd for a di-TMS derivative, m/z 688.3744) by high resolution mass measurement. Negative ion FAB (Fast Atom Bombardment) analysis corroborated the molecular weight assignment (observed $(M-H)^-$, m/z 543).

¹H NMR SPECTRUM

Figure 1:
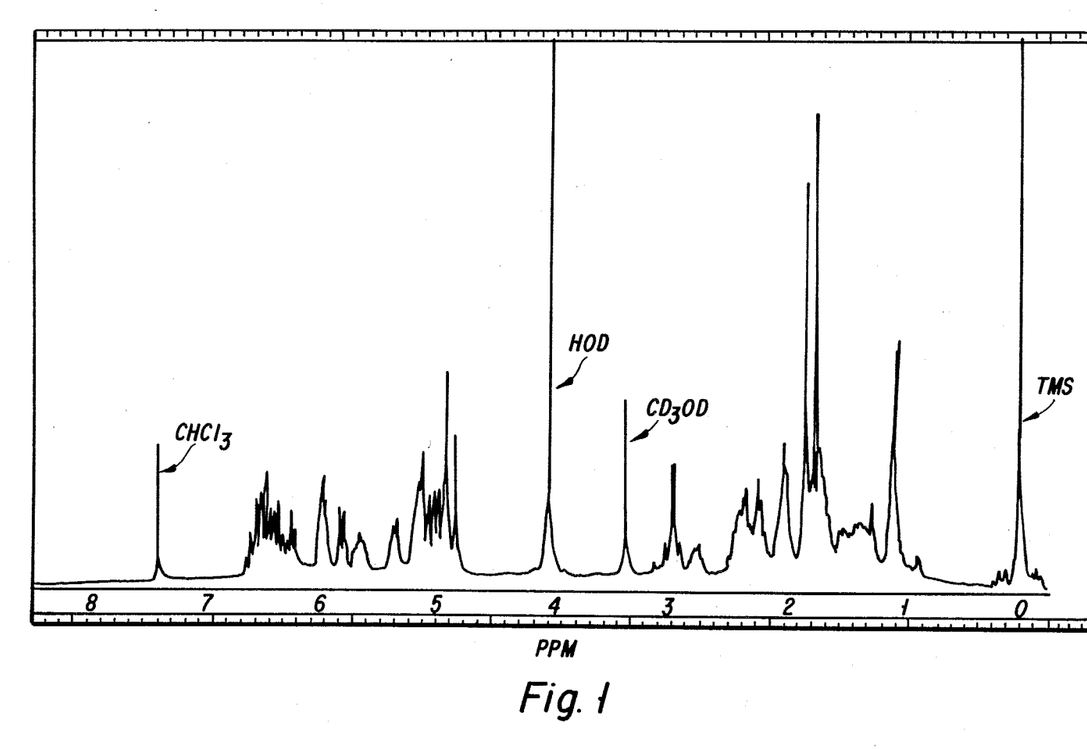

The spectrum is set out as FIG. 1. The spectrum has been recorded at 300 MHz in 20% $CD_3OD/CDCl_3$ at 22° C. (~5 mg/0.35 ml) and chemical shifts are shown in ppm relative to internal tetramethylsilane at zero ppm.

¹³C NMR CHEMICAL SHIFTS

The spectrum was recorded in 20% $CD_3OD/CDCl_3$ at 5° C. Chemical shifts are given in ppm downfield of internal tetramethylsilane (TMS) standard. In agreement with HRMS data, 31 carbon atoms are observed with the following chemical shifts: 16.8, 18.7, 20.0, 23.2, 24.9, 30.7 (2X), 32.7, 35.9, 39.0, 39.5, 41.5, 71.7, 74.2, 111.7, 115.4, 120.7, 123.6, 124.2, 125.0, 126.1, 127.0, 127.2, 129.7, 133.2, 133.7, 134.6, 139.1, 141.1, 146.2, 172.7 ppm.

EXAMPLE 3

Production of Difficidin and Oxydifficidin Using ATCC 39374 Media Preparation Medium A was prepared by suspending the ingredients listed below in distilled water. Fifty milliliters of this suspension was dispensed into 250 ml three-baffled flasks and 500 ml into 2000 ml three-baffled flasks. The flasks were plugged with cotton and autoclaved 30 minutes at 121° C., 18 PSI.

Medium B was prepared by suspending the ingredients listed below in distilled water. The pH was adjusted as indicated and 9.5 liters of this medium was charged into a 14 L New Brunswick Scientific Microferm fermentor, model MF-114. The fermentor was autoclaved, unstirred, at 121° C., 18 PSI, for 120 minutes. Following autoclaving, the medium was mechanically agitated, aerated, and cooled to 28° C.

Medium C was prepared by suspending the ingredients listed below in distilled water, and heating to boiling, and dispensing 12 ml into 18×150 mm tubes. Tubes were autoclaved twenty minutes at 121° C., 18 PSI. Following autoclaving, the tubes were placed at an angle so that the medium would harden into slants.

Culture Preparation

A lyophilized tube of culture ATCC 39374 was inoculated aseptically into a 250 ml three-baffled flask of Medium A and incubated at 220 RPM, 28° C., for 24 hours. This seed culture was used to inoculate 12 slants of Medium C. Once inoculated, the slants were incubated for 96 hours at 28° C., then refrigerated. A portion of the slant prepared as indicated above, was used to inoculate a 250 ml flask of Medium A. The flask was incubated at 220 RPM, 28° C., for 24 hours. Three percent of this first stage seed flask was used to inoculate a 2000 ml flask of medium A which was also incubated at 220 RPM, 28° C., for 24 hours. This second stage seed flask could then be used to either directly inoculate the fermentor or as the inoculum for a third stage seed. If a third stage seed was used, three percent of the second stage seed was used to inoculate another 2000 ml flask of Medium A. Following incubation of the third stage seed at 28° C., 220 RPM for 24 hours, the flask was used to inoculate the fermentor containing Medium B.

Production of Difficidin and Oxydifficidin

The fermentor containing Medium B prepared as described above and inoculated with the previously described second or third stage seed flask, was incubated at 28° C., 300-400 RPM, 0.3 vvm air. Sterile polyglycol P-2000 was added to the fermentor as necessary to control foam; the total amount of polyglycol P-2000 in the fermentor did not exceed 1% (v/v). The fermentation was terminated at 88 hours. Samples withdrawn from the fermentor were extracted with methanol (1 part whole broth plus 2 parts methanol) and assayed by HPLC for product formation. A sample profile, the average of two fermentations, is shown in Table VII. The harvested fermentors were stored at 4°-10° C. until processing.

|  | g/l |
|---|---|
| Medium A: | |
| Trypticase Peptone | 25 |
| Sucrose | 10 |
| Soy Bean Flour | 10 |
| Soluble Starch | 10 |
| CaCO$_3$ | 10 |
| Glucose | 5 |
| Beef Extract | 1 |
| Malt Extract | 1 |
| Yeast Extract | 1 |
| Corn Steep Liquor | 0.5 |
| Soy Bean Oil | 0.1 |
| Trypticase Soy | 0.1 |
| pH 6.8 (as is) | |
| Medium B: | |
| Dextrin | 40 |
| Solulac | 7 |
| Yeast Extract | 5 |
| COCl$_2$—6H$_2$O | 0.05 |
| Polyglycol P-2000 | 5 ml/L |
| pH 7.3 | |
| Medium C: | |
| Agar | 20 |
| Malt Extract | 10 |
| Dextrose | 4 |
| Yeast Extract | 4 |
| pH 7.0 | |

TABLE VII

Activity Profile of 14-Liter Fermentations of Difficidin and Oxydifficidin

| Age (Hours) | Oxydifficidin (mg/l) | Difficidin (mg/l) |
|---|---|---|
| 16 | 9.2 | 12.2 |
| 28 | 25.6 | 61.1 |
| 40 | 27.2 | 61.8 |
| 53 | 41.4 | 116.4 |
| 64 | 46.5 | 132.7 |
| 88 | 55.4 | 149.2 |

These fermentation results are observed to be unusual in that the ratio of difficidin:oxydifficidin produced is about 3:1. More usually this ratio has been observed to be about 1:1.

EXAMPLE 4

Isolation of Difficidin

Approximately 11 L of whole broth (pH 6.5) from the fermentation batch described in Example 3 above was harvested at 88 hours. Broth pH was adjusted to 7.3 with aqueous sodium hydroxide. A 4.8 L portion of isopropanol was added to the broth. After thorough mixing, the broth was clarified by centrifugation. A 14.4 L sample of the clarified broth was adsorbed at 100 ml/min on 1 L of Dowex 1×2 (Cl$^-$) resin, 50-100 mesh. The resin was washed with 2 L of distilled water and eluted at 100 ml/min with 4 L of 3% ammonium chloride in 9:1 methanol-water. Eluate was collected in eight 500 ml fractions. The 1.5 L rich cut (Fractions 2-4) was diluted with 3 L of water and adsorbed at 100 ml/min on a 1 L column of Diaion HP-20 resin. The resin was washed successively with 2 L of 3:7 methanol-water, 1.5 L of 0.1M potassium phosphate pH7, and 2 L of water. Elution of the resin with methanol afforded 2.5 g of 29% pure difficidin. The eluate was concentrated to 30 ml. A 10 ml aliquot (250 mg difficidin) of the concentrate was diluted to 15.4 ml with 0.05M potassium phosphate pH 7.1 to bring the water concentration in the sample to 50% as determined by Karl Fischer analysis. The 15.4 ml sample was chromatographed on 100 ml of Sephadex LH-20 resin in 1:1 methanol-0.05M potassium phosphate pH 7.1. The flow rate was 2.5 ml/min. Difficidin eluted with a retention time of 1.75 column volumes. The 200 ml rich cut was diluted with 150 ml of water and absorbed at 8 ml/min on 80 ml of Diaion HP-20 resin equilibrated in 3:7 methanol-water. The resin was washed with 100 ml of 3:7 methanol-water and eluted with 200 ml of methanol. The eluate rich cut was 80 ml and contained 256 mg of 56% pure difficidin. A 40 ml aliquot of the eluate was concentrated to 4 ml, diluted to 8.2 ml with 0.03M potassium phosphate pH 7, and charged on a 95 ml Whatman Partisil M20 10/25 ODS-3 column (10 micron) that had been equilibrated in 65:35 methanol-0.03M phosphate buffer. The column was eluted with 75:25 methanol-buffer and effluent was collected in a series of 10 ml fractions. Fractions 31 through 40 were combined, concentrated to a solution containing less than 30% methanol, and adsorbed at 2.5 ml/min on 25 mil of Diaion HP-20 resin. The resin was washed with 100 ml of 3:7 methanol-water. Elution with methanol afforded 54 mg of essentially pure difficidin. The antibacterial was stored in methanol at $-80°$ C. to minimize decomposition. Aliquots were lyophilized from water to provide samples for physiochemical characterization. The $^1$H NMR spectrum and mass spectra showed the product to be identical to the product evaluated in Example 2, Step D above.

EXAMPLE 5

Preparation of Oxydifficidin

Three different fermentation procedures were employed in preparing oxydifficidin.

A. Media Preparation

Medium A, described below, was prepared by dissolving the ingredients listed below in distilled water and adjusting the pH to between 7.0 and 7.2 with concentrated HCl or 50% NaOH before sterilization. Fifty ml of this medium was dispensed into 250 ml, 3-baffled shake flasks, and 500 ml of this same medium was dispensed into 2000 ml, 3-baffled shake flasks. The flasks were plugged with cotton, sterilized by heating in an autoclave at 121° C. for 25 minutes, and allowed to cool to room temperature.

| Medium A | |
|---|---|
| Dextrose | 0.1% |
| Soluble starch | 1.0 |
| Beef extract | 0.3 |
| Ardamine pH | 0.5 |
| NZ Amine Type E | 0.5 |
| MgSO$_4$7H$_2$O | 0.005 |
| Phosphate Buffer[1] | 2.0 ml |
| CaCO$_3$[2] | 0.05% |

[1]Phosphate Buffer:
KH$_2$PO$_4$ 9.1%
Na$_2$HPO$_4$ 9.5
pH - 7.70
[2]Added after pH was adjusted to its appropriate level.

Medium B, described below, was prepared in a New Brunswick Scientific nutrient sterilizer, model NS-20, by suspending the ingredients listed below in distilled water, adjusting the pH to between 7.2 and 7.4 with concentrated HCl or 50% NaOH before sterilization, and sterilizing by heating at 121° C., 18 pounds per square inch of pressure, for 20 minutes. Fourteen-liter New Brunswick Scientific magnetically coupled Microferm fermentors, model MF-114, were sterilized with 100 ml distilled water in the jar by heating in an autoclave at 121° C., 18 pounds per square inch of pressure, for 90 minutes. Nine and one-half liters of cooled Medium B from the nutrient sterilizer was aseptically transferred to the sterile fermentors and the temperature adjusted to about 28° C.

| Medium B | |
|---|---|
| Dextrin | 4.0% |
| Distillers Solubles | 0.7 |
| Yeast Extract | 0.5 |
| COCl$_2$.6H$_2$O | 0.005 |

Culture Development

A lyophile of *Bacillus subtilis* ATCC 39320 was opened aseptically and used to inoculate a 250 ml flask of Medium A prepared as indicated above. The flask was incubated at 28° C. for 24 hours on a 220 rpm rotary shaker. Inoculum development continued by aseptically transferring 15 ml from the first flask into each of three 2000 ml shake flasks of Medium A. The 2000 ml shake flasks were incubated at 28° C. for 24 hours on a 220 rpm rotary shaker. Final pH measurements on the seed stages ranged from 7.20 to 8.35.

PRODUCTION

One 2000 ml flask was used to inoculate each of the 14-liter vessels prepared as previously indicated. The fermentor conditions set immediately after inoculation were 28° C. (27.9 to 28.3° C.), 300 rpm, and 2 liters/minute air, corresponding to a Kd$_w$ of $2.35 \times 10^{-4}$ grams.-moles O$_2$/ml/hr/atm. Polyglycol P-2000 was added as necessary during the fermentation to control foam but did not exceed 0.04%. At 77 hours post inoculation, the agitation and air were reduced to 200 rpm and 1 liter/minute, respectively, corresponding to a Kd$_w$ of $1.3 \times 10^{-4}$ gram.moles O$_2$/ml/hr/atm. Fermentors were harvested 89 hours post inoculation. Antibacterial and pH analyses were performed on fermentor filtered broth samples and the data was as follows:

| Age (Hours) | pH | Antibiotic Activity[1] vs *Vibrio percolans* |
|---|---|---|
| 0 | 6.66 | 0 |
| 17 | 7.20 | 26 |
| 29 | 7.22 | 35 |
| 41 | 7.08 | 34 |
| 53 | 7.08 | 35 |
| 65 | 6.65 | 28 |
| 77 | 6.45 | 29 |
| 89 | 6.35 | 29 |

[1]mm zones from ¼" discs, 50 µl/disc.

B. Media preparation and culture development were the same as described above in A.

PRODUCTION

One 2000 ml flask was used to inoculate each of the 14 liter vessels prepared as previously indicated. The fermentor conditions set immediately after inoculation were 28° C. (28.0°–28.3° C.), 300 rpm, and 2 liters/minute air, corresponding to a Kd$_w$ of $2.35 \times 10^{-4}$ grams.-moles O$_2$/ml/hr/atm. Polyglycol P-2000 was added as necessary during the fermentation to control foam but did not exceed 0.04%. Fermentors were harvested 41 hours post inoculation. Antibacterial and pH analyses were performed on fementor filtered broth samples and the data was as follows:

| Age (Hours) | pH | Antibiotic Activity[1] vs Vibrio percolans |
|---|---|---|
| 0 | 6.64 | 0 |
| 17 | 6.40 | 0 |
| 29 | 6.38 | 35 |
| 41 | 6.45 | 32 |

[1] mm zones from ¼" discs, 50 μl/disc.

C. Media preparation was the same as described above in A.

CULTURE DEVELOPMENT

A lyophile of *Bacillus subtilis* ATCC 39320, was opened aseptically and used to inoculate a 250 ml flask of medium A prepared as indicated above. The flask was incubated at 28° C. for 24 hours on a 220 rpm rotary shaker. Inoculum development continued by aseptically transferring 2 ml from the first flask to each of four other 250 ml flasks of Medium A. These four flasks were incubated at 28° C. for 24 hours on a 220 rpm rotary shaker. After 24 hours, the four flasks were pooled and 15 ml was aseptically transferred to each of four 2000 ml shake flasks of Medium A. The 2000 ml shake flasks were incubated at 28° C. for 24 hours on a 220 rpm rotary shaker. Final pH measurements on the seed stages ranged from 7.21 to 8.35.

PRODUCTION

One 2000 ml flask was used to inoculate each of four 14 liter fermentor vessels prepared as previously indicated. The fermentation conditions set immediately after inoculation were 28° C. (27.5°–28.2° C.), 400 rpm, and 3 liters/minute air corresponding to a $Kd_w$ of $3.8 \times 10^{-4}$ grams.moles $O_2$/ml/hr/atm. Polyglycol P-2000 was added as necessary during the fermentation to control foam but did not exceed 0.23%. At 65 hours post inoculation, the agitation was lowered to 200 rpm, reducing the $Kd_w$ to $1.75 \times 10^{-4}$ grams.moles $O_2$/ml/hr/atm. Fermentors were harvested 89 hours post inoculation. The four batches were combined and centrifuged in a batch-fed Sharples centrifuge at 30,000 rpm. The supernatant was recentrifuged twice more, when a clear supernatant was obtained. The cells were discarded and the supernatant retained for further processing. Antibacterial and pH analyses were performed on fermentor filtered broth samples and the data was as follows, averaged for the four 14-liter batches:

| Age (Hours) | pH | Antibiotic Activity[1] vs Vibrio percolans |
|---|---|---|
| 0 | 6.93 | 5.8 |
| 17 | 6.57 | 19.8 |
| 29 | 6.38 | 27.7 |
| 41 | 6.07 | 26.7 |
| 53 | 6.11 | 26.7 |
| 65 | 5.96 | 27.0 |
| 77 | 6.50 | 27.5 |
| 89 | 6.05 | 26.5 |

[1] mm zones from ¼" discs, 50 μl/disc.

EXAMPLE 6

Isolation and Purification of Oxydifficidin

A. Preliminary Purification of Oxydifficidin

Whole broth from four 14 L fermentations, described in Example 5 above, grown under identical conditions, were combined and processed through a turbo Sharples centrifuge. The clear centrifuge, 28.3 L, was adjusted to pH 4.8 with concentrated hydrochloric acid and adsorbed on 2.1 L of Rohm and Haas Amberlite XAD-2 resin. The resin was then washed at the same flow rate with 8 L of water. Antibiotic activity was eluted from the resin with 6 L of ethyl acetate, collected in a single fraction. The elute contained approximately 0.8 L of a dark aqueous lower layer, which was removed and discarded. The ethyl acetate layer was dried briefly with anhydrous sodium sulfate and then concentrated to 400 ml.

The crude antibacterial was back-extracted into water by stirring the ethyl acetate concentrate with 150 ml of $H_2O$ during which the pH of the aqueous layer was brought to 8.5 with 2.5N sodium hydroxide. The aqueous extract was removed and the spent ethyl acetate was again extracted at pH 8.5 with 100 ml of water. After a final third extraction at pH 8.5 with 70 ml of water, the three aqueous extracts were combined and adjusted to pH 8.5. Final volume 360 ml. The sample was stored frozen at $-80°$ C.

B. Isolation of Essentially Pure Oxydifficidin

The combined aqueous extract from Step A above was thawed, concentrated to 205 ml, and buffered with 15 ml of 1M potassium phosphate pH 7. A 215 ml aliquot of this solution was adsorbed on 500 ml of Dianion HP-20 resin at a flow rate of 20 ml/min. The resin was stepwise washed with 1.5 L of water, 1.5 L of 1:1 methanol-0.1M potassium phosphate pH 7, and 1.5 L of 65:35 methanol-0.1M potassium phosphate pH 7. Oxydifficidin was eluted from the resin with 9:1 methanol-water. Effluent was collected in 20 ml fractions and assayed by HPLC. Fractions 20 to 35 were combined and concentrated to 50 ml (I). pH 7.5; 430 mg oxydifficidin by HPLC asay.

A 49 ml aliquot of (I) (421 mg oxydifficidin was charged on a 170 ml column of LiChroprep RP-18 resin (E. Merck, 25–40 micron) in 1:4 methanol-water. The column was first eluted with 250 ml of 1:4 methanol-water at a flow rate of about 3.5 ml/min. Effluent was discarded. The column was then eluted at the same flow rate with 1:1 methanol-water. A series of 20 ml fractions were collected. Based on UV and HPLC assays, Fractions 27 to 38 were combined as essentially pure oxydifficidin. To prevent freezing during storage at $-80°$ C., 100 ml of methanol was added to the fractions to bring the methanol concentration to 65%. Final volume 360 ml containing 378 mg of essentially pure oxydifficidin.

The sample was stored at $-80°$ C. (II).

C. Alkaline Phosphatase Dephosphonylation of Oxydifficidin

TLC System: Whatman $KC_{18}F$ reverse phase plate 9:1 methanol-0.1M sodium citrate pH 6.0.

To a 100 μl aliquot of a 5 mg/ml aqueous solution of oxydifficidin, sample (II) from Step B above, was added 10 μl of 0.25M TRIS hydrochloride buffer pH 8.0 and 5 μl of calf intestinal mucosa alkaline phosphatase (2000 units/ml, P-L Biochemicals, Inc.). After 60 min. incubation at 28° C., the majority of oxydifficidin ($R_f$ 0.59) had been transformed into a new substance ($R_f$ 0.38) which was negative to Hane's Reagent for phosphate detection.

D. Isolation of Essentially Pure Oxydifficidin for Physicochemical and Biological Characterization From fermentation studies with the oxydifficidin-producing organism, described in Example 5 above, three broths were obtained with good antibiotic titer.

| Batch | Whole Broth Volume | pH |
|---|---|---|
| 1 | 6.7 L | 6.3 |
| 2 | 6 L | 6.2 |
| 3 | 7.3 L | 6.1 |

Crude oxydifficidin was isolated from each batch individually by the following procedure. Whole broth (6-7 L) was adjusted to pH 4.8 with concentrated hydrochloric acid. It was found advantageous to centrifuge the broth to remove the cell mass to avoid possible column plugging during the subsequent XAD-2 adsorption step. It was, however, shown possible to adsorb oxydifficidin directly from whole broth onto XAD-2 resin. The broth (clarified or whole) was adsorbed onto 700 ml of Rohm and Haas Amberlite XAD-2 resin, 20-50 mesh at 70 ml/min. The resin was washed with 2.5 L of water. Crude oxydifficidin was eluted with 2.5 L of ethyl acetate. The lower aqueous layer of the ethyl acetate eluate was discarded; the upper layer was dried over anhydrous sodium sulfate and concentrated to ca. 300 ml. The ethyl acetate concentrated was back-extracted at pH 8.5 successively with 100 ml, 50 ml, and 30 ml of water as described in Step B above. The combined aqueous extract was adjusted to pH 6.8 and stored at $-80°$ C.

The aqueous extracts of batches 1, 2, and 3 were each concentrated to 150-200 ml to remove dissolved ethyl acetate and were then combined. The solution was buffered with 10 ml of 1M potassium phosphate pH 7 and adsorbed onto 450 ml of Dianion HP-20 resin at a flow rate of 20 ml/min. The column was washed successively with 1.4 L of 0.1M potassium phosphate pH 7, 1.4 L of 1:1 methanol-0.1M potassium phosphate pH7. The column was then eluted with 9:1 methanol-water at 20 ml/min. Effluent was collected in five fractions (Fr 1-5) with volumes of 220 ml, 100 ml, 200 ml, and 210 ml respectively. Based on HPLC assay and agar disc diffusion assay against *Vibrio percolans*, Fractions 3 and 4 were combined as the oxydifficidin cut (III); ca 350 mg oxydifficidin by HPLC assay.

Sample (III) was concentrated to 45 ml and adjusted to pH 7.0. The concentrate was charged on a column of 170 ml of LiChroprep RP-18 resin (E. Merck, 25-40 micron) in water. The column was first washed with 450 ml of water. The column was then eluted with 600 ml of 1:1 methanol-water, followed by 1.1 L of 65:35 methanol-water. The eluate was collected in 20 ml fractions. Based on UV and HPLC assays, fractions 28-42 were combined. To prevent freezing during storage at $-80°$, 100 ml of methanol was added to the pooled fractions (IV). Volume 380 ml. The sample was lyophilized to afford 238 mg of essentially pure oxydifficidin (V). Stored under nitrogen at $-80°$ C.

E. Physicochemical Characterization of Oxydifficidin (Sample V)

| UV Spectrum (in 0.1 M potassium phosphate) | |
|---|---|
| λMax | $A_{1\,cm}^{1\%}$ |
| 235 nm | 750 |
| 266 nm (sh) | 304 |
| 275 nm | 376 |
| 284 nm (sh) | 307 |

There is evidence that from 10-15% decomposition of oxydifficidin may have occurred during lyophilization of (IV) to (V). Based on the lyophilized weight of (V) and the UV analysis of (IV), $A_{1\,cm}^{1\%}$ (275 nm)—438 is calculated.

MASS SPECTRAL DATA

Electron impact mass spectra (EI-MS) gave $M^+ - H_3PO_4$ ions at m/z 462.3095 corresponding to the formula $C_{31}H_{42}O_3$ (calc'd 462.3134) by high resolution mass measurements. Other significant ions in the high-mass region occur at m/z 444, 381 and 349. Upon trimethylsilylation, the sample exhibited a molecular ion at m/z 776.4100 as a tri-TMS derivative ($M^+$.TMS$_3$) corresponding to the molecular formula $C_{31}H_{45}O_7P$ (MW 560) calc'd for the tri-TMS derivative, m/z 776.4089). Other significant ions and their corresponding exact mass values and elemental formula, confirming the neat EI-MS ions at m/z 462, 381 and 349 as mon-TMS derivatives, are as follows:

| Found | Calcd | Formula* |
|---|---|---|
| 534.3528 | 534.3529 | $C_{31}H_{42}O_3.TMS_1$ |
| 453.2881 | 453.2825 | $C_{25}H_{33}O_3.TMS_1$ |
| 421.2998 | 421.2927 | $C_{25}H_{33}O.TMS_1$ |
| 299.0669 | 299.0720 | $H_3PO_4.TMS_3-CH_3$ |

*TMS = $SiC_3H_8$

$^{13}C$ NMR CHEMICAL SHIFTS

The spectrum was recorded in CD$_3$OD/CDCl$_3$ ($\sim$1:1) at 0° C. (12 mg/0.35 ml). Chemical shifts are given in ppm downfield of internal tetramethylsilane (TMS) standard. In agreement with the mass spectral data, 31 carbon atoms were observed with the following chemical shifts: 16.3, 16.7, 18.8, 24.1, 26.1, 31.3 (2X), 33.5, 36.2, 41.8, 46.6, 72.5, 74.5, 75.2, 114.1, 115.4, 121.3, 124.8, 125.0 (2X), 125.2, 126.6, 127.3, 129.4, 133.9, 134.0, 137.1, 139.0, 141.2, 144.6, 173.5 ppm.

The peaks at 33.5 and 72.5 ppm occur as doublets through coupling to $^{31}P$ of the phosphate group.

$^1H$ NMR SPECTRUM

Figure 2:
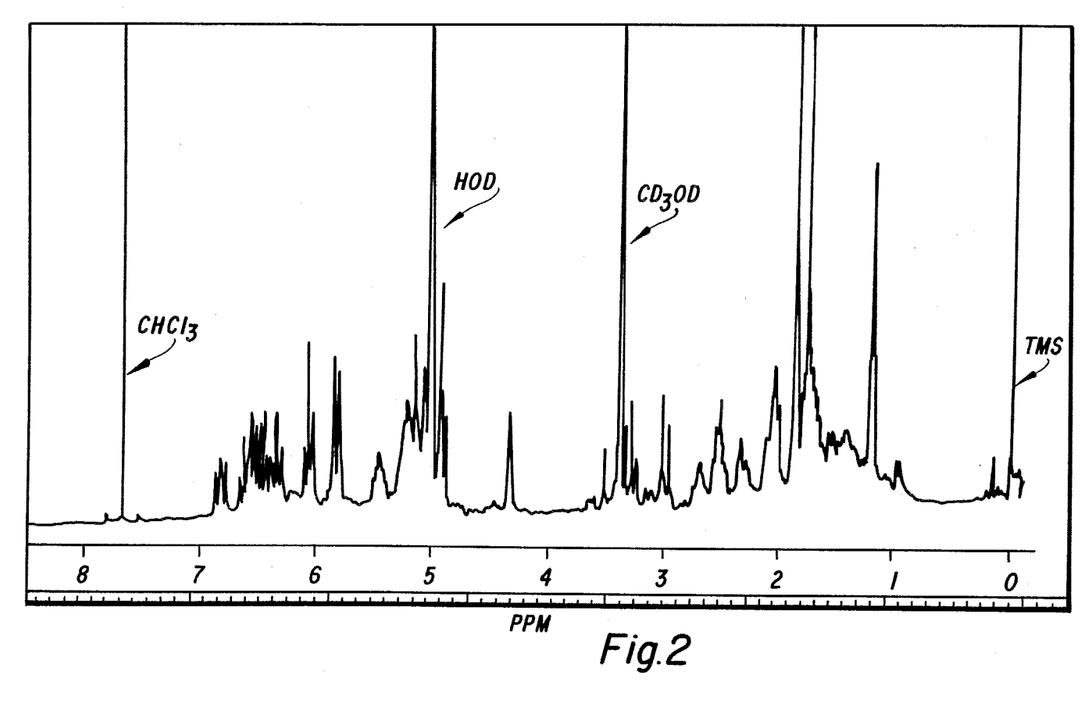

The spectrum is set out as FIG. 2. The spectrum was recorded at 300 MHz in CD$_3$OD/CDCl$_3$ ($\sim$1:1) at 0° C. ($\sim$4 mg/0.35 ml). Chemical shifts are shown in ppm relative to internal tetramethylsilane at zero ppm.

TLC Data

Whatman KC$_{18}$F reverse phase plates
9:1 methanol-0.1M sodium citrate, pH 6.0 $R_f$=0.59
visualization methods
  (1) illumination under short ultraviolet light
  (2) Hane's reagent spray (ammonium molybdate-HClO$_4$) for phosphate esters MS results establish the molecular formula for antibiotic oxydifficidin as $C_{31}H_{45}O_7P$ (MW 560). Facile loss of $H_3PO_4.2TMS$ from the molecular ion of tris(trimethylsilyl)-oxydifficidin suggests the phosphorous atom is present as a phosphate monoester. This is supported by the positive Hane's reagent test (TLC) and by the ready inactivation of oxydifficidin by alkaline phosphatase Step C above. NMR data suggest that the structure of oxydifficidin contains, in addition to the phosphate:

eight olefinic bonds, two of which are terminal methylenes one ester or lactone function one hydroxyl group, and one ring.

What is claimed is:

1. A compound of the formula:

where $R_a$ and $R_b$ are members independently selected from the group consisting of hydrogen; alkali metal and alkaline earth metal cations; ammonium; and substituted ammonium; and $R^1$ is hydrogen or hydroxy.

2. The compound difficidin according to claim 1 wherein $R^1$ is hydrogen.

3. The compound oxydifficidin according to claim 1 wherein $R^1$ is hydroxy.

4. A pharmaceutical composition for inhibiting the growth of bacteria comprising an antibacterially effective amount of a compound according to claim 1 and a pharmaceutically acceptable carrier.

5. A method of treating bacterial infections in mammals which comprises intravenously, intramuscularly, or subcutaneously administering an antibacterially effective amount of a compound according to claim 1.

* * * * *